United States Patent [19]

Nelson

[11] 4,453,004

[45] Jun. 5, 1984

[54] PROCESS FOR THE ALKYLATION OF PHENOLIC COMPOUNDS

[75] Inventor: Randall B. Nelson, Shelton, Wash.

[73] Assignee: International Telephone and Telegraph Corporation, New York, N.Y.

[21] Appl. No.: 364,325

[22] Filed: Apr. 1, 1982

[51] Int. Cl.³ .................... C07C 51/347; C07C 45/61; C07C 41/16

[52] U.S. Cl. .................... 562/473; 568/315; 568/433; 568/648; 564/223

[58] Field of Search ............... 568/433, 648, 312, 315; 562/473; 564/223

[56] References Cited

U.S. PATENT DOCUMENTS

| | | | |
|---|---|---|---|
| 2,490,842 | 12/1949 | Smutz | 568/433 X |
| 2,496,803 | 2/1950 | McMillan | 568/433 |
| 3,007,968 | 11/1961 | Kirkwood | 568/433 |
| 3,367,972 | 2/1968 | Gitchel et al. | 568/433 |
| 3,867,458 | 2/1975 | Imai et al. | 568/433 |
| 4,065,504 | 12/1977 | Findlay | 568/433 |

OTHER PUBLICATIONS

Olson, Jour. Amer. Chem. Soc., vol. 69, (1947), 2451–2454.

Wagner et al., Synthetic Org. Chemistry, (1953), 229, 250–251.

*Primary Examiner*—Bernard Helfin
*Attorney, Agent, or Firm*—James B. Raden; Harold J. Holt

[57] ABSTRACT

A process for the preparation of an alkylated phenolic ether comprising reacting a phenolic compound at a temperature of at least the melting point of the phenol and in the absence of a solvent with an alkylating agent until an alkylated phenol is produced.

21 Claims, No Drawings

PROCESS FOR THE ALKYLATION OF PHENOLIC COMPOUNDS

This invention relates to a process for the preparation of an alkylated phenolic compound from the corresponding phenolic compound.

It is well known that phenols, particularly lignin derived phenols, may be generally alkylated by the use of alkyl sulfates, alkyl halides or alkyl sulfonates in either protic or aprotic solvents. A typical example of such a reaction is shown in *Organic Syntheses*, Collective Vol. II, page 619, 1943, in which veratraldehyde is prepared from vanillin, a lignin derived chemical. The process there shown involves the preparation of an intermediate sodium salt or phenolate with an alkali hydroxide and water as a solvent and the subsequent alkylation of the phenolate with methyl sulfate to produce the alkylated phenol. This process is similar to those employed in the chemical industry for the production of veratraldehyde from vanillin.

The known process is, however, expensive and troublesome. For example, the alkylating agent used in the process must be a very reactive alkyl halide or sulfate. Some of the alkylating agent often undergoes hydrolysis in the solvent, is wasted, and therefore excess quantities are required. The alkylating agents, e.g. dimethyl sulfate or methyl chloride, are themselves acutely toxic and require special handling procedures.

Another disadvantage of the known process lies in its preparation and use of the intermediate phenolate Na+ or K+ salt. The preparation and reaction of these salts requires the use of solvents. Water is inexpensive but its use as a solvent often causes competing hydrolytic reactions leading to impure alkylated products. Also, from an economic viewpoint, the use of solvent reduces the amount of reagents, either phenol or alkylating agent, that can be put into the reactor. Therefore the throughput of the reaction suffers leading to increased man-hours per pound of product.

It is accordingly a primary object of the present invention to increase the throughput of alkylation reactions of phenolic compounds, to improve the quality of the final product and to avoid the necessity for the use of hazardous chemical reactants.

It is a more specific object of the invention to provide an alkylation process for phenolic compounds which does not require the use of a solvent and does not require the production of an intermediate alkali metal phenolate.

The foregoing and other objects of the invention are achieved in a process for the preparation of an alkylated phenolic ether which comprises preparing a reaction mixture comprising a phenolic compound and an alkylating agent, the alkylating agent being selected from the group consisting of an alkyl ester and an alkyl halide, and reacting the mixture in the absence of a solvent at a temperature of at least the melting point of the phenol until an alkylated phenol ether is produced.

The present process is an improvement over known processes of reacting the phenolic constituent with an alkali hydroxide and reacting the resulting phenolate with an alkylating agent. The present process is a melt phase reaction. Alkylation of the phenol is performed at or above its melting point which obviates the necessity of preparing the alkali metal phenolate and therefore the use of solvent.

In carrying out the invention, it is desirable to use a small amount of a base catalyst. The reaction proceeds without a catalyst but at a very reduced reaction rate. Any base may be used that neutralizes acid such as an alkali metal or alkaline earth hydroxide, an amine, ammonia or trisodium phosphate. However, the alkylation reaction does not require heavy excesses of a base nor does is require a strong base. A strong alkaline catalyst may be used but less than a molar equivalent of the strong alkaline catalyst will be necessary. It is preferred to use a weak alkaline catalyst and a preferred class of such catalysts are carbonate salts such as sodium, potassium, magnesium or calcium carbonate. The small amount of carbonate required for the reaction under normal pressure is between 0 and 10 mole percent, based on the total moles of reactant phenolic compound, although larger amounts are not deleterious. Amounts as small as 0.1 mole will sometimes be adequate. Since there is no solvent, the alkylating agent cannot be taken up by any other reactant and hydrolytic side reactions are avoided. This leads to considerably improved product quality.

The starting phenolic compound will normally be a lignin derived mono- or polycyclic phenol. The reaction may generally be represented by the following equation showing the conversion of the phenolic compound into the corresponding ether:

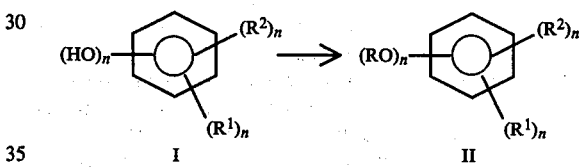

In the formulae above, $R^1$ and $R^2$ may be the same or different and are a radical selected from the group consisting of H, OH, alkyl, alkenyl, cycloalkyl, alkoxy, aryl, halogen and a carbonyl radical such as an aldehyde, ketone, ester, amide and acid, at least one of $R^1$ and $R^2$ preferably being $—COR^3$ where $R^3$ is hydrogen, an alkyl, cycloalkyl or aryl radical. R is a one to four carbon atom alkyl group. n is from one to four. Where $R^1$ or $R^2$ is aryl, it may be attached to a single carbon atom of the phenolic nucleus (to form a biphenyl, for example) or it may share two carbon atoms to form a polycyclic phenol (as for ex., naphthalene compounds). The orientation of the radicals may be varied in the ortho, meta or para position with respect to the —OH group and with respect to each other.

In the final alkylated product, the —OH group, or groups, are substituted with the alkyl moiety of the alkylating agent to become the corresponding ether of the starting compound.

Examples of phenolic compounds falling within the above formula I are such monohydric phenols as phenol and o, m and p-cresol; phenolic aldehydes such as protocatechualdehyde, vanillin, syringaldehyde, p-hydroxybenzaldehyde, 5-formylvanillin and salicylaldehyde; phenolic ketones such as p-hydroxyacetophenone, acetovanillone, acetosyringone, acetamidophenol and guaiacol; and phenolic acids such as vanillic acid, syringic acid and p-hydroxybenzoic acid. The preferred phenolic reactants are those having at least one carbonyl functionality.

The alkylating agent may be essentially any compound which is a source of a one to four carbon atom alkyl group. It may be either a gas or a liquid. In general, the alkylating agents may be alkyl sulfonates such as methyl and ethyl p-toluenesulfonate and methyl and ethyl benzenesulfonate; trialkyl phosphates such as trimethyl and triethyl phosphate; and dialkyl sulfites such as dimethyl and diethyl sulfite. The use of dialkyl sulfites as alkylating agents in the one step process is novel and is the subject of my copending application Ser. No. 364,327 filed of even date herewith. The use of trialkyl phosphates as alkylating agents is also novel and is the subject of my copending application Ser. No. 364,326 also filed of even date herewith. The disclosure of these applications is hereby incorporated by reference. Other alkylating agents which may be used are alkyl sulfates such as dimethyl sulfate, diisopropyl sulfate and diethyl sulfate; alkyl halides such as methyl chloride, methyl bromide, methyl iodide, ethyl chloride, ethyl bromide, ethyl iodide and similar propyl and butyl halides.

In the process of the invention it is usually advantageous to choose an alkylating agent which has a boiling point several degrees higher than the melting point of the phenol being alkylated to control pressure surges during the course of the reaction. For this reason the trialkyl phosphates are especially advantageous since their boiling points are generally much higher than the melting point of the phenolic compound. The process should be carried out at at least at atmospheric pressure and preferably at a positive pressure.

The method of the invention is especially suitable for the manufacture of methylated and ethylated lignin derived phenolics which have hitherto been prepared commercially by use of the very much more hazardous diethyl and dimethyl sulfates or methyl and ethyl halides. The method of the invention allows the use of chemicals not previously considered capable of efficient high yield alkylation of phenols such as trimethyl phosphate and triethyl phosphate and offers a measure of safety in the chemical industry hitherto unavailable. The alkylating agent need not be added in excess, however a slight molar excess is preferable.

In a preferred embodiment of the process of the invention, a lignin derived phenol is melted and contacted with an alkali carbonate and an alkylating agent which provides the alkyl radical for the formation of the final alkylated product—a phenol ether. The lignin derived phenol is melted under an inert atmosphere and a small amount of the alkali carbonate is added. Alternatively, the carbonate may be added before melting is initiated. The alkylating agent is added progressively, i.e., incrementally as the reaction progresses, so as to keep the reaction temperature near the initial feed temperature, i.e., about 5° to 10° C. above the melting point of the phenol, until a slight stoichiometric excess (the preferred amount is usually about 1.2 molar equivalents of alkylating agent relative to phenol) of alkylating agent has been added. After addition of alkylating agent, the temperature is maintained for a brief period (i.e., several hours) to insure completion of reaction and then the mixture is cooled to a moderate (e.g., 50° C.) temperature and drowned in water. Total reaction time is normally from 1 to 10 hours. The product can be collected directly or, if an oil, can be extracted into a suitable organic solvent and recovered in a manner familiar to those skilled in the art. Alternatively, the oil itself may be separated from the drowned reaction mixture and purified by one of several known standard methods such as fractional distillation. For many purposes, however, the crude product is of sufficient purity (often 95% assay) for use directly in the intended product.

The following examples illustrate the practice of the invention. Unless otherwise indicated, all parts and percentages are by weight.

EXAMPLE 1

In a three-neck flask (capacity 100 ml) equipped with a mechanical stirrer and reflux condenser, 5.00 g (0.033 mol) of vanillin and 5.00 g (0.036 mol) of anhydrous potassium carbonate were placed and the mixture was heated under a nitrogen atmosphere to 85° C. The mixture was a clear to amber melt of vanillin with carbonate in suspension. To this mixture was added 5.00 ml (0.043 mol) of trimethyl phosphate over about 5 minutes while maintaining the reaction temperature below 125° C. The mixture was maintained at about 80° C. for one hour and then cooled to 40° C. The mixture was poured into 20 ml water and extracted two times with 20 ml of methylene chloride. The combined extracts were dried over anhydrous potassium carbonate, filtered, and concentrated to give 5.4 g (99%) of veratraldehyde as a pale oil.

EXAMPLE 2

In an apparatus similar to Example 1, 15.0 g (0.099 mol) of vanillin and 10.0 g (0.072 mol) of anhydrous potassium carbonate were heated under nitrogen to 90° C. To this clear slurry was added over about 10 minutes 13.5 ml (0.112 mol) of trimethyl phosphate while holding the temperature below 110° C. The mixture was stirred and heated to 65°-75° C. for three hours then cooled to 35° C. and quenched with 80 ml of water to precipitate an oil. On stirring a light powder precipitated which was filtered, washed with three 100 ml portions of water, and dried to give 13.3 g (81%) of veratraldehyde.

EXAMPLE 3

In an apparatus as in Example 1, 10.0 g (0.054 mol) of syringaldehyde and 5.00 g (0.036 mol) of potassium carbonate were heated to 100° C. and 8 ml (0.094 mol) of dimethyl sulfite was added over a 5 minute period. The pasty mixture was heated to 100° C. for 3 hours then cooled to 25° C. and quenched with 50 ml water. The mixture was extracted with 100 ml of methylene chloride. The extracts were washed with water and concentrated in vacuo to get 4.2 g (54% based on recovered syringaldehyde) of 3,4,5-trimethoxybenzaldehyde.

EXAMPLE 4

In an apparatus similar to Example 1, 15.2 g (0.083 mol) of syringaldehyde and 15.0 g (0.11 mol) of potassium carbonate were heated to 105° C. under nitrogen and 15 ml (0.12 mol) of trimethyl phosphate were added over 10 minutes. The mixture was maintained at about 80° C. for 3 hours then cooled to 45° C. and quenched with 50 ml of $H_2O$. The tan solid which precipitated was collected, washed with $3 \times 50$ ml of water and dried to give 15 g (92%) of 3,4,5-trimethoxybenzaldehyde.

EXAMPLE 5

This example illustrates the alkylation of p-acetamidophenol to produce p-acetamidoanisole.

To a three-necked 100 ml flask equipped for reflux and fitted with a mechanical stirrer was added 10.0 g (0.066 mol) of p-acetamidophenol, 2.0 g (0.014 mol) of potassium carbonate, and 20 ml (0.17 mol) of trimethyl phosphate. The mixture was heated to 90° C. for three hours then allowed to stand overnight before quenching with 50 ml of water. Extraction into methylene chloride and removal of residual starting material via a base wash with 6% sodium hydroxide solution gave on concentration in vacuo 6.5 g (60%) of p-acetamidoanisole.

EXAMPLE 6

This example illustrates the preparation of salicylaldehyde from o-methoxybenzaldehyde.

To a three-necked 100 ml flask equipped for reflux and fitted with a mechanical stirrer was added 5.0 mol (0.047 mol) of salicylaldehyde, 2.0 g (0.014 mol) of potassium carbonate, and 10.0 ml (0.085 mol) of trimethyl phosphate. The mixture was heated to 85° C. for two hours, then cooled to 50° C. and quenched with 20 ml of water. After two hours the mixture was extracted with 50 ml of methylene chloride, the extracts washed with dilute caustic and then water. The organic extracts were dried over anhydrous potassium carbonate then filtered and concentrated in vacuo to give 3.6 g (53%) of o-methoxybenzaldehyde.

EXAMPLE 7

This example illustrates the preparation of veratric acid methyl ester from vanillic acid.

To a three-necked 100 ml flask equipped for reflux and fitted with a mechanical stirrer was added 2.0 g (0.012 mol) of vanillic acid, 2.0 g (0.0072 mol) of potassium carbonate, and 10 ml (0.085 mol) of trimethyl phosphate. The mixture was heated to 70° C. for five hours then cooled and quenched with 25 ml of water. The organic portion was extracted into 50 ml of methylene chloride. The extract was washed with dilute sodium hydroxide solution to remove all partially alkylated material and then was washed once with water, dried over anhydrous potassium carbonate, filtered, then concentrated in vacuo to give 1.8 g (77%) of veratric acid methyl ester.

EXAMPLE 8

This example illustrates the preparation of p-acetamidoanisole from p-acetamidophenol.

To a three-necked 100 ml flask equipped for reflux and fitted with a mechanical stirrer was added 10 ml (0.12 mol) of dimethyl sulfite, 2.0 g (0.014 mol) of potassium carbonate, and 5.0 g (0.033 mol) of p-acetamidophenol. The mixture was heated to 70° C. for six hours then quenched while hot with 50 ml of water. The solution was made basic with dilute caustic and the organic materials were extracted into methylene chloride. The extracts were concentrated in vacuo to give 2.0 g (73%) of p-acetamidoanisole (based on recovered starting material).

EXAMPLE 9

This example illustrates the preparation of veratraldehyde from protocatechualdehyde.

To a three-necked 100 ml flask equipped for reflux and fitted with a mechanical stirrer was added 1.0 g (0.0072 mol) of protocatechualdehyde 1.0 g (0.007 mol) of potassium carbonate, and 4.0 ml (0.074 mol) of dimethyl sulfite. The mixture was heated for four hours then quenched hot with 25 ml of water. The organic material was extracted into methylene chloride and the extracts were washed with 15 ml of 12% caustic solution, 25 ml of water and then concentrated in vacuo to obtain 0.5 g (42%) of crude veratraldehyde.

EXAMPLE 10

This example illustrates the preparation of veratric acid methyl ester from vanillic acid.

To a three-necked 100 ml flask equipped for reflux and fitted with a mechanical stirrer is added 1.0 g (0.006 mol) of vanillic acid, 1.0 g (0.007 mol) of potassium carbonate, and 4.0 ml (0.047 mol) of dimethyl sulfite. The mixture was heated to 70° C. for three hours then quenched while hot with 15 ml of water. The organics were extracted into 25 ml of methylene chloride, washed with 15 ml of 12% caustic and then washed with water. The extracts were dried over anhydrous $K_2CO_3$, filtered and concentrated in vacuo to get 0.8 g (68%) veratric acid methyl ester.

EXAMPLE 11

This example illustrates the preparation of methyl p-methoxybenzoate from p-hydroxybenzoic acid.

To a 100 ml three-necked flask equipped for reflux and fitted with a mechanical stirrer was added 2.0 g (0.014 mol) of p-hydroxybenzoic acid, 1.0 g (0.007 mol) of potassium carbonate, and 5.0 ml (0.059 mol) of dimethyl sulfite. The mixture was heated at 100° C. for four hours and then quenched with 15 ml of water. The organics were taken up with methylene chloride and washed sequentially with 12% caustic solution and water. The extracts were concentrated in vacuo to give 1.28 g (55) of methyl p-methoxybenzoate.

It will thus be apparent that an alkylation process has been provided which, by performing the reaction in the melt, permits vessel throughput to become limited only by the volume of the reactants used since no diluent or solvent is required. The absence of solvent means that costs of purchase, recovery and purifications of solvent are avoided. Moreover the melt-phase reactivity of the phenolic compounds, and particularly the phenolic carbonyl compounds, is such that milder bases and weaker alkylating agents become very reactive and in this way a large excess of alkylating agent can be avoided.

I claim:

1. A process for the melt phase preparation of an alkylated phenolic ether comprising
   heating a phenolic compound to a temperature of at least its melting point and
   reacting said melted phenolic compound with an alkylating agent selected from the group consisting of an alkyl ester and an alkyl halide in the absence of a solvent and in the presence of a base catalyst at a temperature of at least the melting point of the phenolic compound until an alkylated phenol ether is produced.

2. The process of claim 1 in which the catalyst is a carbonate salt selected from the group consisting of sodium, potassium, magnesium and calcium carbonate.

3. The process of claim 1 in which the phenolic compound is a phenolic carbonyl compound.

4. The process of claim 3 in which the phenolic compound is a monocyclic phenolic aldehyde.

5. The process of claim 4 in which the phenolic compound is selected from the group consisting of vanillin, syringaldehyde, salicylaldehyde and protocatechualdehyde.

6. The process of claim 5 in which the phenolic compound is vanillin.

7. The process of claim 5 in which the phenolic compound is syringaldehyde.

8. The process of claim 3 in which the phenolic compound is a monocyclic phenolic ketone.

9. The process of claim 8 in which the phenolic compound is acetamidophenol.

10. The process of claim 3 in which the phenolic compound is a monocyclic phenolic acid.

11. The process of claim 10 in which the phenolic compound is selected from the group consisting of vanillic acid and p-hydroxybenzoic acid.

12. The process of claim 1 in which the alkylating agent is an alkyl halide.

13. The process of claim 12 in which the alkyl halide is selected from the group consisting of methyl and ethyl halides.

14. The process of claim 1 in which the alkylating agent is an alkyl ester.

15. The process of claim 14 in which the alkyl radical of the ester is selected from the group consisting of methyl and ethyl and the ester radical is selected from the group consisting of sulfate and sulfonate.

16. The process of claim 1 in which the alkylated phenol is separated by precipitation directly from the reaction mixture.

17. The process of claim 1 in which the alkylated phenol is separated by extraction from the reaction mixture.

18. The process of claim 1 in which the alkylating agent is added to the melted phenolic compound as the reaction progresses.

19. A process for the preparation of an alkylated phenolic ether comprising
heating a phenolic carbonyl compound to a temperature above its melting point,
adding to said phenolic compound a slight stoichiometric excess of an alkylating agent selected from the group consisting of an alkyl ester and an alkyl halide and reacting said alkylating agent with said phenolic compound in the presence of from 0.1 to 10 mole percent of a carbonate salt while the temperature of the reaction is maintained above the melting point of the phenolic compound,
maintaining the temperature of the reaction mixture until the alkylation reaction is complete,
cooling the reaction mixture and
separating an alkylated phenol ether.

20. The process of claim 19 in which the phenolic carbonyl compound is vanillin and the alkylated phenolic ether is veratraldehyde.

21. The process of claim 19 in which the phenolic carbonyl compound is syringaldehyde and the alkylated phenolic ether is 3,4,5-trimethoxybenzaldehyde.

* * * * *